(12) United States Patent
Deming et al.

(10) Patent No.: US 6,506,577 B1
(45) Date of Patent: Jan. 14, 2003

(54) SYNTHESIS AND CROSSLINKING OF CATECHOL CONTAINING COPOLYPEPTIDES

(75) Inventors: Timothy J. Deming, Summerland, CA (US); Miaoer Yu, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/272,682

(22) Filed: Mar. 19, 1999

Related U.S. Application Data (60) Provisional application No. 60/078,590, filed on Mar. 19, 1998.

(51) Int. Cl.[7] .......................... C12P 21/06; C08G 63/48; C08L 89/00; C07K 1/00
(52) U.S. Cl. ....................... 435/68.1; 435/28; 435/195; 525/54.1; 525/54.11; 106/124.1; 106/124.3; 106/160.1; 530/211; 530/338; 530/343; 530/402; 530/407
(58) Field of Search ............................. 435/68.1, 281, 435/195; 525/54.1, 54.11; 106/124.1, 124.3, 160.1; 530/211, 338, 343, 402, 407

(56) References Cited

U.S. PATENT DOCUMENTS

| | | | |
|---|---|---|---|
| 4,496,397 A | * | 1/1985 | Waite .......................... 106/161 |
| 4,585,585 A | | 4/1986 | Waite .................. 260/112.5 R |

OTHER PUBLICATIONS

Linder, Elek., Biol. Mar. Comun. Congr. Int. Corros. Mar. Incrustaciones, 5th (1980), pp. 189–212, Ed. Garasi: Madrid, Spain.*
Filpula et al., *Biotechnol. Prog.*, vol. 6, No. 3, pp. 171–177, 1990.*
Yamamoto et al., *Journal of Colloid and Interface Science*, vol. 156, pp. 515–517, 1993.*
Crisp et al., *Journal of Colloid and Interface Science*, vol. 104, No. 1, pp. 40–50, Mar. 1985.*
Nagai et al., *Bull. Chem. Soc. Jpn.*, vol. 62, No. 7, pp. 2410–2412, 1981.*
Varlender et al., *Proc. Nat. Acad. Sci, USA*. vol. 73, No. 4, pp. 1009–1013, Apr. 1976.*
Yu et al., *J. Am. Chem. Soc.*, vol. 121, No. 24, pp. 5825–5826, 1999.*
Filpula, D. R.; Lee, S.–M.; Link, R. P.; Strausberg, S. L.; Strausberg, R. L. *Biotechnol. Prog.*, 1990, 6, 171.
Saez, C.; Pardo, J.; Gutierrez, E.; Brito, M.; Burzio, L. O. *Comp. Biochem. Physiol.*, 1991, 98B, 569–572.
J.H. Waite, *Biol. Bull.*, 183:178–184 (1992).
J.H. Waite, *Comp. Biochem. Physiol.*, 97B:19 (1990).
J.H. Waite, *Biol. Rev.*, 58:209–231 (1983).
A. Nagai, et al., *Bull. Chem. Soc. Japn.*, 62:2410–2412 (1989).
H. Yamamoto, et al., *Macromolecules*, 16:1058–1063 (1983).
H. Yamamoto, et al., *Biopolymers*, 21:1137–1151 (1982).
H. Yamamoto, et al. *Biopolymers*, 18:3067–3076 (1979).
J. H. Waite, *Journal of Biological Chemistry*, 258:2911–2915 (1983).
L.M. Rzepecki, et al., *Archives of Biochemistry and Biophysics*, 285:17–26 (1991).
D. J. Crisp et al., *Journal of Colloidal & Interface Science*, 104:40–50 (1985).
M. Olivieri, et al., *Biomaterials*, 13:1000–1008 (1992).
T. Williams, et al., *Archives of Biochemistry and Biophysics*, 269:415–422 (1989).
P. Nagy, et al., *Int.J.Peptide Protein Res*, 38:84–89 (1991).
S. W. Taylor et al., *J. Am. Chem. Soc.*, 116:10803–10804 (1994).
A. Salerno et al., *Appl. Microbiol. Biotechnol.*, (1993).
Papov et al., *Journal of Biological Chemistry*, 270:20183–20192 (1995).
Klug, et al., *Archives of Biochemistry and Biophysics*, 333:221–224 (1996).
V. Vreeland, et al., *J. Phycol*, 34:1–8 (1998).
J. H. Waite, *Journal of Adhesion Society of Jpn*, 33:186–193 (1997).
H. Yamamoto, et al. *Polymers*, 18:979–983 (1978).
H. Yamamoto, et al. *Polymers*, 19:963–968 (1978).
*Journal of Colloid & Interface Science*, 156:515–517 (1993).

* cited by examiner

Primary Examiner—Christopher S. F. Low
Assistant Examiner—Abdel A. Mohamed
(74) Attorney, Agent, or Firm—Fulbright & Jaworski L.L.P.

(57) ABSTRACT

The synthesis of moisture-resistant adhesive polypeptides, conditions for their use, and conditions for controlling characteristics of the crosslinked matrix are disclosed. By specifically manipulating the conditions under which these networks are formed, the characteristics of the networks may be precisely regulated. These manipulatable adhesive networks are water-based, show exceptional bonding capabilities toward wet materials (including biological tissues), and have a variety of biotechnological applications.

14 Claims, 2 Drawing Sheets

| Organism | MW | Consensus peptide |
|---|---|---|
| *Phragmatopoma californica* | 35 kD | ValGlyGlyDOPAGlyDOPAGlyAlaLys |
| *Mytilus edulis* | 130 kD | AlaLysProSerTyrdiHypHypThrDOPALys |
| *Geukensia demissa* | 130 kD | ThrGlyDOPAGlyProGlyDOPALys |
| *Aulacomya ater* | 130 kD | AlaGlyDOPAGlyGlyLeuLys |
| *Dreissena polymorpha* | 76kD | GlyProDOPAValProAspGlyProTyrAspLys |
| *Brachidontes exustus* | 105kD | GlyLysProSerProDOPAAspProGlyDOPALys |

SYNTHESIS AND CROSSLINKING OF CATECHOL CONTAINING COPOLYPEPTIDES

CROSS-REFERENCE TO RELATED APPLICATIONS

This application is a non-provisional application under 37 CFR 1.15(b) claiming priority under Section 119(e) to provisional application No. 60/078,590, filed Mar. 19, 1998, the contents of which is hereby incorporated by reference.

STATEMENT REGARDING FEDERALLY FUNDED RESEARCH

This invention was made with Government support under Grant No. N00014-96-1-0729, awarded by the Office of Naval Research and Grant No. DMR-9123048, awarded by the National Science Foundation. The Government has certain rights in this invention.

BACKGROUND OF THE INVENTION

1. Field of the Invention

The present invention relates to adhesive copolymers modeled on bioadhesive proteins secreted by marine organisms. These copolymers are compatible with the metabolism, growth and function of living tissues and/or cells in vitro or in vivo and, consequently, are suitable for use in a wide variety of biomedical applications.

2. Description of Related Art

Polymeric materials have been widely used for implants or other biomedical applications, since they bear close resemblance to natural tissue components such as collagen, which allows direct bonding with other substances. Decades of peptide research have created a wide variety of biomedically useful polypeptides. However, they still are the most underrated and underused polymers considering their impressive properties, which include infusibility, mechanical strength and adhesive capability due to a highly flexible backbone and many functional side chains. Waite, et al., *Science*, 212:1038–1040 (1981) identified some of nature's most powerful adhesives, bioadhesive polyphenolic proteins, secreted by marine mussels which live under water and routinely cope with the forces of surf and tides. The naturally-occurring bioadhesive polyphenolic protein is produced and stored in the exocrine phenol gland of the mussel and is deposited onto marine surfaces by the mussel's foot during the formation of new adhesive plaques. While the natural bioadhesive polyphenolic protein can be extracted and purified according to the procedures set forth in the *Journal of Biological Chemistry*, 258:2911–2915 (1983) or U.S. Pat. No. 4,496,397, the utility of the natural bioadhesive polyphenolic protein extracted from the mussel is limited by the quantities that can be obtained. Consequently synthetic polymers of these natural bioadhesive proteins have been the focus of a significant amount of research, particularly for their potential use as surgical tissue adhesives.

Decades of investigation into this field has led to the discovery of many different marine organisms which secrete adhesive materials. These organisms include many varieties of mussels, which have different environmental needs and subsequent uses for the adhesives they produce, but are alike in that the materials they use for adhesion and cementing contain many of the same building blocks and apparently operate by the same mechanism. See e.g. J. H. Waite, et al., *J. Comp. Physiol. B*, 159:517–525 (1989) and L. M. Rzepecki, et al., *Mol. Mar. Biol. Biotech.*, 2:255–279 (1993).

The adhesive proteins isolated from mussels (e.g., Mytilus edulis) have been purified and examined for use as tissue adhesives. Preliminary experiments indicated that these proteins are very effective for formation of adhesive bonds to animal tissues and also exhibit low immunogenicity. See e.g. J. H. Waite, *Polym. Prepr.*, 30(1):181–182 (1990) and C. Saez, et al., *Comp. Biochem. Physiol.*, 98B:569–572 (1991). The major drawbacks with these materials are that (i) their mechanisms of action are poorly understood, (ii) the essential requirements for good adhesion and crosslinking are unknown, (iii) recombinant proteins must be enzymatically treated to generate post-translationally modified residues (i.e. DOPA), and (iv) these proteins cannot be produced inexpensively or in the large quantities necessary for successful commercial application. See e.g. J. H. Waite, *Biol. Rev.*, 58:209–231 (1983) and C. V. Benedict, et al., *ACS Symp. Ser.*, 385:465–483 (1989).

Figure 1:
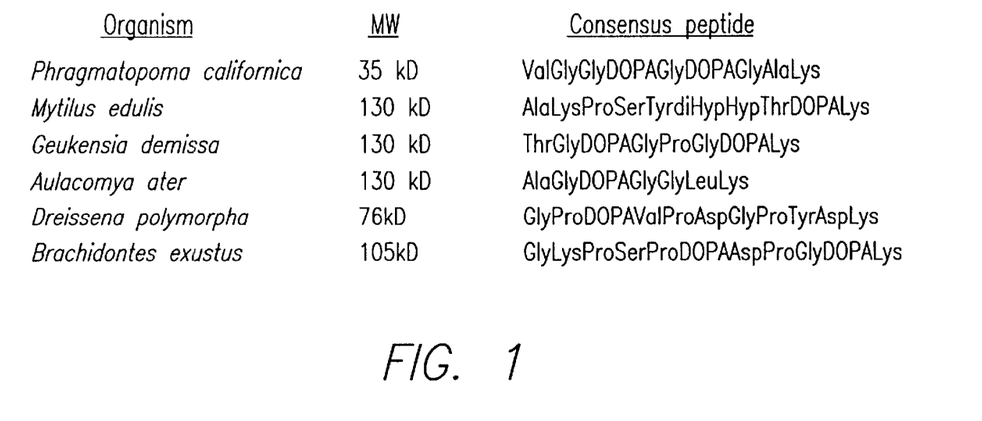
FIG. 1 shows sequences of various naturally occurring marine adhesive proteins.
Figure 2:
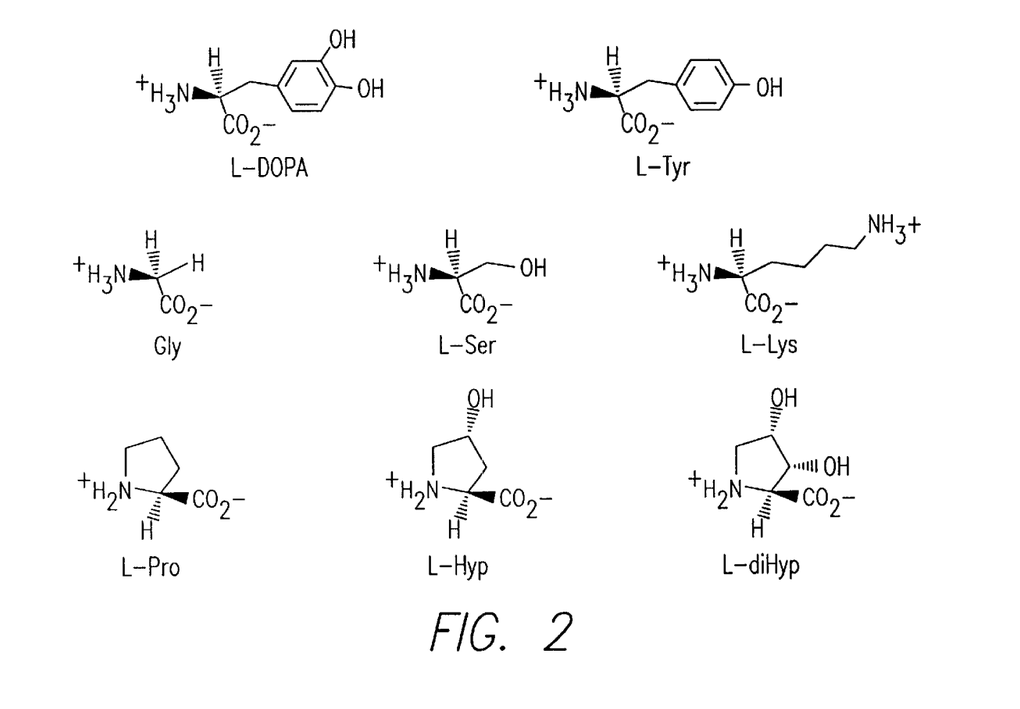
FIG. 2 shows various amino acid structures found in adhesive proteins.

The adhesive precursor proteins have been isolated and sequenced from a wide variety of organisms and are known to show certain characteristics. A partial list of these proteins is given in FIG. 1. Examples of amino acid structures found in adhesive proteins are provided in FIG. 2. It is important to note that these consensus repeats are just that, and that considerable variation is present in the sequence of each protein. The repetitive polypeptides have basic isoelectric points (due to lysine residues), flexible conformations (due to high percentages of small glycine and serine residues), and high levels of the amino acid 3,4-dihydroxyphenyl-L-alanine (DOPA). See e.g. J. H. Waite, et al., *Science*, 212:1038–1040 (1981) and J. H. Waite, *J. Biol. Chem.*, 258:2911–2915 (1983). The DOPA residues are believed to be primarily responsible for (i) chemisorption of the polymers to surfaces underwater and (ii) covalent cross-linking or setting of the adhesive. J. H. Waite, *Comp. Biochem. Physiol.*, 97B:19 (1990); J. H. Waite, *Biol. Bull.*, 183:178–184 (1992).

A number of groups have studied the bioadhesive qualities of synthetic peptides modeled upon marine adhesive proteins. Yamamoto, et al. report the synthesis of L-DOPA homopolymer as well as copolymers of L-DOPA with L-lysine and L-glutamic acid. H. Yamamoto, et al., *Polymer*, 19:1115–1117 (1978); H. Yamamoto, et al., *Macromolecules*, 16:1058–1063 (1983); H. Yamamoto, et al., *Biopolymers*, 21:1137–1151 (1982); H. Yamamoto, et al. *Biopolymers*, 18:3067–3076 (1979). They have also reported random L-lysine/L-tyrosine copolymers, and the synthesis of complex random copolypeptides which contain as many as 18 different amino acids, including L-DOPA. H. Yamamoto, et al., *Int. J. Biol. Macromol.*, 12:305–310 (1990); A. Nagai, et al., *Bull. Chem. Soc. Japn.*, 62:2410–2412 (1989); H. Yamamoto, et al., *Mar. Chem.*, 37:131–143 (1992); H. Yamamoto, et al., *Mar. Chem.*, 26:331–338 (1989). Sequentially specific copolymers between L-DOPA and L-lysine or L-glutamic acid were prepared by stepwise condensation procedures. Random copolymers of L-DOPA and L-glutamic acid were prepared by polymerization of N-carboxyanhydride (NCA) monomers. Benedict et. al. at Biopolymers, Inc. have also reported synthetic polymers which were composed of small L-DOPA containing peptides grafted to polyamine backbones. C. B. Benedict, et al., U.S. Pat. No. 4,908,404, Mar. 13, 1990. The materials were reported to form adhesive bonds to a variety of substrates and were found to work well with phosphate buffers.

Studies on a variety of synthetic polypeptides modeled upon marine adhesive proteins indicate that these molecules are promising candidates for use as bioadhesives. H.

Yamamoto, *J. Chem. Soc. Perkin Trans. I,* 613–918 (1987). Additional studies disclose an analysis of adhesive properties of L-lysine/L-tyrosine random copolymers and complex random copolymers where tyrosinase enzyme was used as an oxidizing agent. H. Yamamoto, et al., *Int. J. Biol. Macromol.,* 12:305–310 (1990); A. Nagai, et al., *Bull. Chem. Soc. Japn.,* 62:2410–2412 (1989). These adhesive systems were, however, studied under limited reaction environments such as water and diluted synthetic seawater and were found to form adhesive bonds to iron and $Al_2O_3$.

In order to facilitate the commercial applications of synthetic peptides modeled upon marine adhesive proteins, there is a need for methods to precisely control the material aspects of the adhesive matrix. In particular, such controlled manipulation of adhesive polypeptide characteristics such as curing time and adhesive strength have a wide number of applications in different biomedical and related commercial contexts. Unfortunately, while the manipulation of adhesive polypeptide characteristics have a number of biomedical applications, specific methods of controlling the material properties of these molecules have not been disclosed.

SUMMARY OF THE INVENTION

To address the need for methods to control the crosslinking of synthetic peptides modeled upon marine adhesive proteins, we disclose methods which allow us to synthesize and manipulate the characteristics of copolypeptides which contain the side-chain functional groups (e.g. catechol and primary amine) that are present in these natural adhesive proteins. Specifically, we examined a range of different copolymers to illustrate the effects of a number of factors on crosslinking behavior including the oxidizing agent, copolypeptide concentration and composition and sequence of the functional groups. By controlling the conditions of the reaction environment under which the peptides are crosslinked, it is possible to optimize a variety of different material characteristics of the crosslinked catechol containing copolypeptide adhesive matrix.

The synthetic adhesives disclosed herein are useful since they are water based and thus do not require the use of hazardous or expensive organic solvents for their application. They are also able to form adhesive bonds to a variety of wet surfaces where nearly all commercial synthetic adhesives fail to form strong bonds. The materials disclosed herein are readily prepared and production can easily be scaled to large quantities, an important consideration when these materials are compared with recombinant or natural marine adhesive proteins which possess similar properties, but which are more expensive. These materials may find use as surgical tissue adhesives, dental adhesives, bone cements, hemostatics, as well as other biomedical and industrial applications involving moisture-resistant adhesion.

This disclosure describes the synthesis of moisture-resistant adhesive polypeptides, conditions for their use, and example applications. Illustrative polypeptides containing the amino acid L-dihydroxyphenylalanine (L-DOPA) were prepared as copolymers with L-lysine, L-glutamic acid, L-serine, L-alanine to give water soluble copolymers. Aqueous solutions of these copolymers, when mixed with various oxidizing agents (including $O_2$, mushroom tyrosinase, $Fe^{3+}$, $H_2O_2$, ROOR, and $IO_4^-$), formed crossirinked networks which were found to form moisture-resistant adhesive bonds to a variety of substrates (including aluminum, $Al_2O_3$, iron, glass, wood, and plastics). The novel features of this system are that the adhesive components are water-based, the polymers are derived from biological sources and may be biocompatible/biometabolizable, the polymers show exceptional bonding capabilities toward wet materials including biological tissues, and the copolymers can be readily prepared in large quantities. The methods disclosed herein are represented by a number of embodiments. One embodiment provides a method of crosslinking a catechol containing polypeptide including the steps of exposing the catechol containing polypeptide to a reaction environment and controlling a condition within the reaction environment to modulate a characteristic of the crosslinked catechol containing polypeptide. In a variation of this embodiment a second condition within the reaction environment is controlled to further modulate a characteristic of the crosslinked catechol containing polypeptide. In one embodiment of these methods, the catechol containing polypeptide is a synthetic polypeptide.

In a typical embodiment of these methods, the characteristic of the crosslinked catechol containing polypeptide is modulated by controlling a factor within the reaction environment selected from the group consisting of oxidizing agent, pH, temperature and polymerization time. In a preferred embodiment, the crosslinked catechol containing polypeptide is modulated by controlling an oxidizing agent, which can be an enzyme like mushroom tyrosinase, or an inorganic chemical, such as $O_2$, $H_2O_2$, $NaIO_4$ and $Fe(H_2O)_6^{3+}$. In yet another embodiment, the characteristic of the crosslinked catechol containing polypeptide is modulated by controlling a factor within the reaction environment selected from the group consisting of polypeptide monomer composition, polypeptide molecular weight, and polypeptide concentration.

In preferred embodiments, the characteristic of the crosslinked catechol containing polypeptide that is modulated is selected from the group consisting of adhesive strength, gellation time and viscosity. In an illustrative embodiment of these methods, the adhesive strength is modulated by controlling the substrate with which the crosslinked catechol containing polypeptide interacts, for example aluminum, steel or glass.

In related embodiments, the invention disclosed herein provides methods of modulating a characteristic of a crosslinked catechol containing polypeptide including modulating at least one factor within the crosslinking reaction environment, wherein the characteristic is selected from the group consisting of adhesive strength, gellation time and viscosity. In a typical embodiment of a method directed to modulating adhesive strength, the factor within the crosslinking reaction environment that modulates adhesive strength is selected from the group consisting of pH, temperature, oxidizing agent, curing time, polypeptide monomer composition, polypeptide molecular weight, polypeptide concentration and substrate with which the crosslinked catechol containing polypeptide interacts. In a typical embodiment of a method directed to modulating viscosity or gellation time or both viscosity and gellation time, the factor within the crosslinking reaction environment that modulates these characteristics is either the oxidizing agent utilized in the crosslinking reaction, the pH or both oxidizing agent and the pH.

By utilizing synthetic polymers, our disclosure can avoid the complexities associated with synthesis and analysis of natural proteins by use of peptides and polymers which contain only the minimal functional groups necessary for cement formation. Concurrent polymer synthesis coupled with characterization has lead to a rapid convergence of crosslink mechanism determination and discovery of the essential adhesive components. Simplified materials also allow the design and synthesis of marketable adhesives prepared through low cost, high volume polymerization techniques.

Using known compositions of many natural adhesive proteins, we prepared sequentially random copolypeptides through copolymerization of a few select α-amino acid N-carboxy anhydrides (NCAs). H. R. Kricheldorf, α-*Amino acid-N-Carboxyanhydrides and Related Heterocycles,* Springer-Verlag, New York, (1987). NCAs are readily prepared from amino acids by phosgenation and can be polymerized into high molecular weight polypeptides via successive ring opening addition reactions which liberate carbon dioxide. A similar approach for making adhesive polymers using NCA polymerizations has been reported by Yamamoto and coworkers. A. Nagai, et al., *Bull. Chem. Soc. Japn.,* 62:2410–2412 (1989); H. Yamamoto, et al., *Int. J. Biol. Macromol.,* 12:305–310 (1990); H. Yamamoto, *J. Chem. Soc. Perkin Trans. I,* 613–918 (1987). They have prepared random copolypeptides containing the amino acids Glutamic acid, DOPA, Tyrosine, and Lysine, as well as a complex mixture of 17 different NCAs. H. Yamamoto, et al., *Mar. Chem.,* 26:331–338 (1989); H. Yamamoto, et al., *Mar. Chem.,* 37:131–143 (1992). Their work was focused on conformational analyses of the polymers and there was no attempt to determine the amount of moisture resistance in adhesion measurements. Furthermore, the adhesive roles of the catechol versus the oxidized o-quinone functionalities of DOPA were not separately evaluated.

Figure 3:
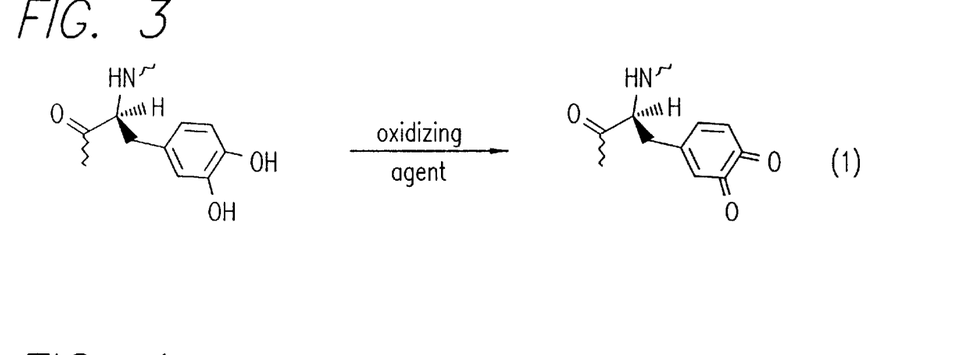
FIG. 3 is a schematic representation of an oxidizing agents' conversion of catechol functionalities of DOPA residues into o-quinone units which are believed to be responsible for a variety of crosslinking reactions.

We disclose methods of manipulating simple catechol containing copolypeptides having different compositions. These polymers were found to be soluble in aqueous buffers over wide pH ranges (ca 2–12). Further, we disclose methods involving the manipulation of polymer crosslinking conditions as functions of a number of factors such as monomer composition, pH, and the specific oxidizing agent utilized in the crosslinking reaction. The different oxidizing agents are shown to vary in their conversion of the catechol functionalities of the DOPA residues into o-quinone units, the units which are believed to be responsible for a variety of crosslinking reactions. J. H. Waite, *Polym. Prepr.,* 30(1):181–182 (1990); J. H. Waite, *Biol. Rev.,* 58:209–231 (1983). A illustration of an illustrative oxidizing agent reaction is provided in FIG. 3. By varying the conditions of the reaction environment, we illustrate systems where the characteristics of the polymer matrix are readily manipulated. In particular, by controlling the crosslinking reaction environment, gellation times could be adjusted from seconds to hours, and viscosity and adhesive strength could be controlled.

DETAILED DESCRIPTION OF THE INVENTION

Definitions

The term "catechol containing copolypeptide" is used herein to refer to polypeptides having a ortho-dihydroxyphenyl (catechol) functional group as side-chain substituents on the polymer backbone, which is comprised of polyamide repeat units.

The term "reaction environment" is used herein to broadly refer to the variety of reagents and reaction conditions which can influence the crosslinking and characteristics of a crosslinked catechol containing polypeptide. Such conditions include, but are not limited to variables such as temperature, pH, oxidizing agents and the duration of exposure to the different variables within this environment. Moreover, such conditions include polypeptide monomer composition, polypeptide molecular weight, polypeptide concentration and the substrate with which a crosslinked polypeptide interacts.

Figure 4:
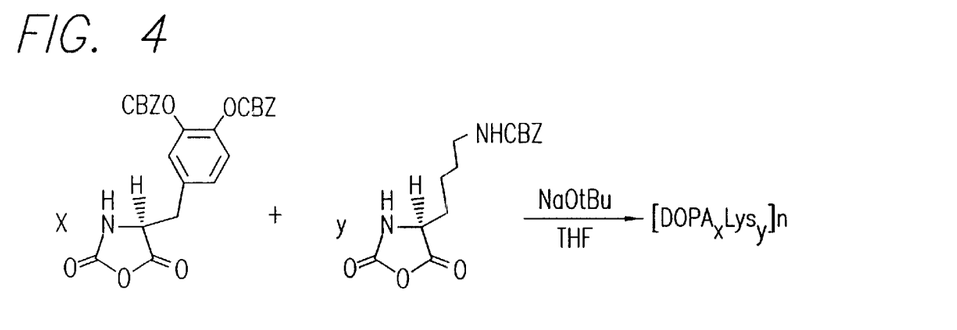
FIG. 4 is a schematic representation of the preparation of adhesive copolypeptides using NCA monomers.
Figure 5:
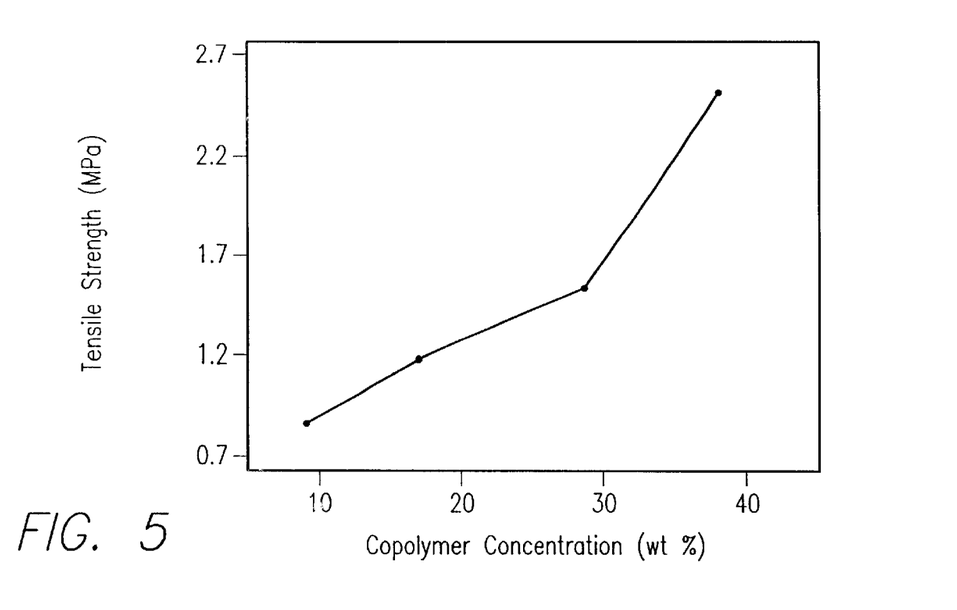
FIG. 5 is a graph of Lap Shear vs. Polymer concentration. Showing adhesive strength as a function of copolymer concentration for 8($M_n$=98,000) on steel at 40° C. after 1 day cure time.

The term "crosslinking" when used herein refers to the chemical conversion of catechol functionalities of DOPA residues into o-quinone units which then self-condense to form extensively crosslinked intractible solids Synthesis of Catechol Containing Copolypeptides In the examples below, we disclose the design and synthesis of simplified adhesive polymers which incorporate the essential functional components of the marine proteins. Using the known compositions of many natural adhesive proteins, we have prepared sequentially random copolypeptides through copolymerization of a few select α-amino acid N-carboxy anhydrides (NCAs). This reaction is illustrated in FIG. 4. H. R. Kricheldorf, α-*Amino acid-N-Carboxyanhydrides and Related Heterocycles,* Springer-Verlag, New York, (1987). NCAs are readily prepared from amino acids by phosgenation and can be polymerized into high molecular weight polypeptides via successive ring opening addition reactions which liberate carbon dioxide. This approach is similar to that utilized by Yamamoto et al., supra.

As illustrative examples of catechol containing adhesive polymers, we prepared simple copolypeptides of L-lysine and L-DOPA containing different compositions of the two monomers. We also prepared copolymers of L-DOPA with L-glutamic acid, L-serine, and L-alanine. Deprotection of copolypeptides containing L-glutamic acid was accomplished using iodotrimethylsilane (or chlorotrimethylsilane and sodium iodide) in methylene chloride; the remainder of the copolypeptides were deprotected using HBr in acetic acid. G. A. Olah, et al., *J. Org. Chem.,* 44:1247–1251 (1979). Unless otherwise indicated, preparation of the α-amino acid-N-carboxyanhydrides of di-(O-CBZ)-L-dihydroxyphenylalanine (di-(O-CBZ)-L-DOPA), ε-(N-CBZ)-L-Lysine, (OBz)-L-Serine, and L-Alanine were performed either in a $N_2$ filled dry box or on a Schlenk line according to literature procedures. H. R. Kricheldorf, α-*Amino Acid-N-Carboxyanhydrides and Related Heterocycles,* Springer-Verlag, New York, (1987). These monomers were recrystallized until free of halide and were stored at −10° C. under nitrogen until used. Unless otherwise indicated, polymerization reactions of the above α-amino acid-N-carboxyanhydrides were run in THF under $N_2$ atmosphere in sealed vessels using NaOtBu initiator at 25° C. for 2 days. Tandem gel permeation chromatography/light scattering (GPC/LS) was performed on a Spectra Physics Isochrom liquid chromatograph pump equipped with a Wyatt DAWN DSP light scattering detector and Wyatt Optilab DSP. Separations were effected by $10^5$ Å, $10^4$ Å, and $10^3$ Å A Phenomenex 5 μm columns using 0.10 M LiBr in DMF as eluent. NMR spectra were recorded on Bruker AMX 500 MHz and Varian Gemini 200 MHz spectrometers.

Crosslinking of Catechol Containing Copolypeptides

Disclosed herein are methods of crosslinking catechol containing copolypeptides comprising exposing the catechol containing copolypeptides to a reaction environment under controlled conditions to optimize a characteristic of the crosslinked matrices. The reaction environment may be manipulated by the control of single variables or by controlling a combination of variables. By manipulating the conditions in the reaction environment in this manner, crosslinked catechol containing copolypeptide matrices having specific characteristics may be generated.

In one embodiment of the invention, the conditions of the reaction environment are controlled by exposing a catechol containing copolypeptide to a specific oxidizing agent. Examples of oxidizing agents that are useful variables in the reaction environment include an enzyme like mushroom tyrosinase, or an inorganic chemical, such as $O_2$, $O_2$/base, $NaIO_4$, $H_2O_2$, and $Fe(H_2O)_6^{3+}$. In another embodiment of the invention, the conditions of the reaction environment are controlled by exposing a catechol containing copolypeptide to a specific pH scheme. In yet another embodiment of the invention the conditions of the reaction environment are controlled by exposing a catechol containing copolypeptide to various factors within the reaction environment for varying lengths of time. In additional embodiments, the characteristics of the crosslinked matrices can be optimized by controlling other reaction variables including the specific monomer components within the polypeptide, or the polymer concentration. The characteristics of the crosslinked matrices that can be optimized by controlling the conditions of the reaction environment include gellation time, viscosity and adhesive strength.

In one embodiment of the invention, the characteristic that is optimized by controlling the reaction environment is gellation time. For example, the gellation time can be manipulated controlling the type of oxidizing agent present in the reaction environment. In a related embodiment, the gellation time can be manipulated controlling the pH of the reaction environment. In a more specific embodiment, the gellation time can be manipulated exposing a specific copolymer composition (for example Poly-L-Lys$^9$Dopa$^1$ or Poly-L-Lys$^4$Dopa$^1$) to tyrosinase, $NaIO_4$ or $H_2O_2$ at a pH range of 7 to 12.

In another embodiment of the invention, the characteristic that is optimized by controlling the reaction environment is viscosity. For example, the viscosity can be manipulated controlling the type of oxidizing agent present in the reaction environment. In a related embodiment, the viscosity can be manipulated controlling the pH of the reaction environment. In a more specific embodiment, the viscosity can be manipulated exposing a specific copolymer composition to tyrosinase, $NaIO_4$ or $H_2O_2$ at a pH range of 7 to 12.

In another embodiment of the invention, the characteristic that is optimized by controlling the reaction environment is adhesive strength. For example, the adhesive strength can be manipulated controlling the type of oxidizing agent present in the reaction environment. In a related embodiment, the adhesive strength can be manipulated controlling the pH of the reaction environment. In a more specific embodiment, the adhesive strength can be manipulated exposing a specific copolymer composition to tyrosinase, $NaIO_4$ or $H_2O_2$ at a pH range of 7 to 12.

In another embodiment, the adhesive strength can be manipulated controlling a combination of factors including the polymer concentration and the type of oxidizing agent present in the reaction environment. In a specific embodiment, the adhesive strength can be manipulated by exposing copolymer at concentrations including 0.40 g/ml or 0.8 g/ml to the oxidizing agent $H_2O_2$.

In another embodiment, the adhesive strength can be manipulated controlling a combination of factors including the polymer composition, the pH and the type of oxidizing agent present in the reaction environment. In a specific embodiment, the adhesive strength can be manipulated by exposing copolymer compositions (for example Poly-L-Lys$^9$Dopa$^1$ or Poly-L-Lys$^4$Dopa$^1$) at different concentrations (for example 0.40 g/ml or 0.8 g/ml) to the oxidizing agents $O_2$, $O_2$ and base, phosphate buffer ($O_2$-pH=7), tyrosinase, $Fe(H_2O)_6^{3+}$ or $H_2O_2$ at a pH range of 7–12.

In another embodiment, the adhesive strength can be manipulated controlling a combination of factors including the polymer concentration and the type of oxidizing agent present in the reaction environment. In a specific embodiment, the adhesive strength can be manipulated by exposing copolymer at concentrations including 0.40 g/ml or 0.8 g/ml to the oxidizing agent $H_2O_2$.

In other embodiments, the adhesive strength can be manipulated controlling a combination of factors including the polymer substrate, the concentration of the oxidizing agent present in the reaction environment, the temperature of the reaction environment. In one embodiment, the adhesive strength can be manipulated by exposing copolymer at a concentration of 0.40 g/ml to aluminum, steel or plastic substrates at 40° C. for 24 hours. In a related embodiment, copolymer adhesive strength can be manipulated by exposing copolymer at a concentration of 0.40 g/ml to aluminum, and varying concentrations of the oxidizing agent $H_2O_2$. In another related embodiment, copolymer adhesive strength can be manipulated by exposing copolymers to steel, and varying the temperature of the reaction environment or the time the polymer is exposed to conditions within the reaction environment. In yet another embodiment, copolymer adhesive strength can be manipulated by varying the concentration or copolymers composition to steel, and by varying the temperature of the reaction environment.

In another embodiment of the invention, the characteristic that is optimized by controlling the reaction environment is adhesive strength. The characteristic of the crosslinked catechol containing copolypeptides is optimized by controlling the temperature of the reaction environment.

Illustrations of the different embodiments are provided in Examples 3–8 below. Copolymers were tested under a variety of oxidizing conditions and were found to form moisture-resistant adhesive bonds under all conditions. The use of chemical oxidants allowed bond formation in a matter of seconds, while enzymatic and aerobic oxidation gave cured samples in hours and days. Using dilute hydrogen peroxide we were able to form adhesive bonds to aluminum adherends which increased in strength with polymer concentration.

Measurements on different adherents with our optimized conditions also showed formation of moisture-resistant bonds. The best systems for adhesive formation are partially substrate specific. Polymer containing 20 mole percent L-DOPA generally gives the strongest bonds, especially when dissolved in phosphate buffer (0.25M). $H_2O_2$ is generally the best oxidizing agent, except that low concentrations need to be used on metals and plastics, or when slow oxidation is desired.

The examples disclosed herein also provide means to test how various reaction environments will effect the characteristics of the crosslinked polypeptide. Specifically, using the protocols discussed below, a new condition or combination of conditions may be evaluated for their effects on crosslinking and the characteristics of the crosslinked matrices.

As discussed in Example 4 below, the rheological behavior of solutions of the adhesive copolymers under different conditions can studied using art accepted methods. The experiments described herein utilize a Rheometrics ARES Rheometer at room temperature. R. W. Whorlow, *Rheological Techniques, Halsted Press* (1980). Briefly, a cone and plate geometry can be used in a dynamic time sweep experiment at a frequency of 2.0 rad/s and at 100% strain. The viscosity of each adhesive mixture solution can then be measured as a function of time. The two time points are the beginning of the experiment and the gelation point.

As discussed in Example 5 below, the adhesive strength of copolymers generated under different conditions can be studied using art accepted methods. Briefly, tensile strength can be measured with an Instron 1123 Mechanical Testing Apparatus. An Instron 5000 Lb reversible load cell was used for the measurements in the disclosed studies. Adherends for lap shear studies can be prepared in a number of ways. For example aluminum adherends (5052-H32) can be treated with a mixture of water, $H_2SO_4$ (conc.) and $Na_2Cr_2O_7$ (40:20:4) at 65~70° C. for 20 minutes, rinsed with deionized water and air dried. In order to prepare to test a sample preparation, the adhesive polymer solution can be spread on both adherend slides, which were then overlapped with two Cu wires (0.06 mm diameter) placed as spacers between the adhesive joint. The overlapped samples can then be clamped together to prevent motion and kept in a temperature controlled oven for the specified time period. The tensile strength of samples prepared in this manner can be measured at room temperature with an Instron 1123 Mechanical Testing Apparatus according to the ASTM D1002 method.

The basic adhesive system described herein is very flexible with regard to many parameters including: percentage of L-DOPA in the polymers, addition of other amino acids to the copolymers, use of D-amino acids in the polymers, concentration of the polymers in solution, composition of the buffers used to dissolve the polymers, as well as oxidizing agent and concentration. Illustrative examples of this invention include copolypeptides containing L-DOPA and L-Lysine used in combination with chemical oxidizing agents to give an adhesive mixture. The use of various chemical oxidizing agents under different conditions with copolypeptides containing L-DOPA is a new element of this invention.

The advantages of the adhesive materials disclosed herein are (i) the synthetic polymers can be readily and inexpensively prepared in larger quantities than biologically derived materials, (ii) the polymers are able to form moisture-resistant adhesive bonds which rival those of natural marine adhesive proteins, (iii) the lysine containing copolymers have enhanced water solubility and stronger adhesive capabilities, and (iv) the use of various conditions and oxidizing agents allow the control of polymer curing and the optimization of adhesive strength. The parameters described herein are for purposes of example only and variations of the disclosed methods are within the scope of this invention.

EXAMPLES

The following examples are offered by way of illustration and not by way of limitation. The disclosures of all citations in the specification are expressly incorporated herein by reference into this application in order to more fully describe the state of the art to which this invention pertains.

Example 1

General Protocols

Tandem gel permeation chromatography/light scattering (GPC/LS) was performed on a Spectra Physics Isochrom liquid chromatograph pump equipped with a Wyatt DAWN DSP light scattering detector and Wyatt Optilab DSP. Separations were effected by $10^5$ Å, $10^4$ Å, and $10^3$ Å Phenomenex 5 mm columns using 0.10 M LiBr in DMF as eluent. NMR spectra were recorded on a Varian Gemini 200 MHz spectrometer. A Mettler TA3000 thermal analysis system was used for TGA measurements on the polymers. All IR samples were prepared on NaCl plates and IR spectra were recorded on a Perkin Elmer model 1615 FTIR. Elemental analyses were performed by the Marine Science Institute Laboratory at the University of California, Santa Barbara. L-DOPA (99%), benzyl chloroformate (97%), $N_e$-carbobenzyloxy-L-lysine (98%), L-alanine, sodium hydride, t-butanol and 33 wt. % hydrobromic acid in glacial acetic acid (Technical grade) were obtained from Acros Organics. O-benzyl-L-serine and mushroom tyrosinase were obtained from Sigma Chemical Co. Phosgene was purchased from Fluka. Phosphorous pentachloride (95%) was obtained from Aldrich Chemical Co. Hexanes and THF were distilled from sodium/benzophenone in an inert atmosphere and stored under nitrogen. Sodium t-butoxide was prepared following a literature procedure.

Generation of Amino Acid N-carboxyanhydrides

As illustrated below, $N_e$-carbobenzyloxy-L-lysine N-carboxyanhydride, L-alanine N-carboxyanhydride, and O-benzyl-L-serine N-carboxyanhydride, were prepared by using phosgene following art accepted procedures. A. M. Felix, et al., *J. Medicinal chem.*, 17:422–426 (1974); M. Bodanszky, et al., *The practice of Peptide Synthesis*, $2^{nd}$ Ed. Springer: Berlin Heidelberg (1994); H. Yamamoto, et al., *Biopolymers*, 16:1593–1607 (1977). O,O'-dicarbobenzoxy-L-DOPA N-carboxyanhydride, was prepared from N,O,O'-tricarbobenzoxy-L-DOPA and phosphorus pentachloride following art accepted procedures.

To generate $N_e$-carbobenzyloxy-L-lysine N-carboxyanhydride, $N_e$-Carbobenzyloxy-L-Lysine (6.42 g, 22.4 mmol) was stirred in 125 ml dry THF and phosgene in toluene (15 ml, 29 mmol) was added. The mixture was stirred at room temperature until all the solid dissolved. After stirring an additional 5 hours, the solvent was removed by vacuum to give a white solid. The crude product was recrystalized from THF/hexane to give white crystals (6.48 g, 21.2 mmol, 95%), m.p. 96° C. IR ($CHCl_3$) 1855 $cm^{-1}$, 1784 $cm^{-1}$. $^1H$ NMR ($CDCl_3$) d 1.43 (m, 4H), 1.65 (m, 2H), 3.10 (t, 2H), 4.16 (t, 1H), 4.90 (s, 1H), 5.01 (s, 2H), 6.95 (s, 1H), 7.26 (s, 5H).

To generate O,O'-Dicarbobenzyloxy-L-Dopa-N-carboxyanhydride, L-Dopa (3.00 g, 15.1 mmol) was mixed with 1N NaOH (17 ml, 17 mmol) and 50 ml of $H_2O$, then the mixture was stirred while submerged in an ice-salt bath. Benzyl chloroformate (7.0 ml, 49 mmol) in 25 ml diethyl ether and 2N NaOH (25 ml, 50 mmol) were added simultaneously into the mixture in four portions over a period of one hour. After stirring an additional 1 hour at 0° C. and 2 hours at room temperature, three layers were observed. The bottom colorless layer was isolated and washed with diethyl ether, then acidified to pH=3 with 1M citric acid. The mixture was extracted with diethyl ether (2×100 ml), and the organic layer was washed with water (2×50 ml), dried over $MgSO_4$, and evaporated under vacuum to give a white crystalline solid (7.3 g, 12.2 mmol, 80%), which was used without further purification. $^1$H NMR (CDCl$_3$) d 2.85–3.30 (m, 2H), 4.65 (dd, 1H), 5.09 (s, 2H), 5.17 (s, 2H), 5.19 (s, 2H), 6.98–7.60 (m, 18H). The crude product was,)dissolved in dry tetrahydrofuran (THF, 100 ml) and the solution was stirred while submerged in an ice-water bath. Phosphorous pentachloride (2.94, 13.4 mmol) was added and the mixture was stirred at an ice bath until all the PCl$_5$ dissolved and the IR spectrum of the reaction mixture showed complete conversion to NCA (IR:1859 cm$^{-1}$ and 1787 cm$^{-1}$). The solvent was removed under vacuum to give a slightly yellow oil. The oily product was recrystallized three times from THF/toluene/hexane to give pale yellow crystals of NCA (4.4 g, 9.0 mmol, 73%). Further recrystalization gave white crystals which melt at 60–61° C. $^1$H NMR (CDCl$_3$) d 2.90 (dd, 1H), 3.25 (dd, 1H), 4.42 (dd, 1H), 5.20 (s, 2H), 6.10 (s, 1H), 7.06–7.45 (m, 13H).

Example 2

Generation of Adhesive Copolypeptides

Simple copolypeptides of L-lysine and L-DOPA containing different compositions of the two monomers were prepared using art accepted procedures. H. Yamamoto, et al., *Int. J. Biol. Macromol.*, 12:305–310 (1990); A. Nagai, et al., *Bull. Chem. Soc. Japn.*, 62:2410–2412 (1989). We also prepared copolymers of L-DOPA with L-glutamic acid, L-serine, and L-alanine. The molecular weight of the polymers was obtained by gel permeation chromatography (GPC). Deprotection of copolypeptides containing L-glutamic acid was accomplished using iodotrimethylsilane (or chlorotrimethylsilane and sodium iodide) in methylene chloride; the remainder of the copolypeptides were deprotected using HBr in acetic acid. G. A. Olah, et al., *J. Org. Chem.*, 44:1247–1251 (1979).

Poly(N$_e$-carbobenzyloxy-L-lysine$_4$-O,O'-dicarbobenzyloxy-L-DOPA$_1$) was generated in the following manner. To a mixture of N$_e$-carbobenzyloxy-L-lysine N-carboxyanhydride (1.1 g, 3.7 mmol) and O,O'-dicarbobenzoxy-L-DOPA N-carboxyanhydride (0.46 g, 0.93 mmol) in THF (15 ml) in a Schlenk tube, 0.1N sodium t-butoxide in THF (0.11 ml, 0.019 mmol) was added with stirring. The mixture was stirred for one day at room temperature, then one day at 40° C. and finally four hours at 80° C. The product was precipitated by addition of ether and then dried in vacuo at room temperature overnight to give white polymer (1.22 g, 87%). GPC: M$_n$=186,000, M$_w$/M$_n$= 1.35. $^1$H NMR (TFA-d) d 7.58–7.30 (br m, —(NHCH ((CH$_2$)$_3$CH$_2$NHCOOCH$_2$C$_6$H$_5$)C(O))$_4$—(NHCH(CH$_2$C$_6$H$_3$(OCOOCH$_2$C$_6$H$_5$)$_2$)C(O))$_1$—, 6.6H), 5.26 (br s, —(NHCH ((CH$_2$)$_3$CH$_2$NH—COOCH$_2$C$_6$H$_5$)C(O))$_4$—(NHCH(CH$_2$C$_6$H$_3$(OCOOCH$_2$C$_6$H$_5$)$_2$)C(O))$_1$—, 2.4H), 4.70(br s, —(NHC H((CH$_2$)$_3$CH$_2$NHCOOCH$_2$C$_6$H$_5$)C(O))$_4$—(NHCH(CH$_2$C$_6$H$_3$(OCOOCH$_2$C$_6$H$_5$)$_2$)C(O))$_1$—, 1H), 3.28 (br s, —(NHCH ((CH$_2$)$_3$CH$_2$NHCOOCH$_2$C$_6$H$_5$) C(O))$_4$—(NHCH(CH$_2$C$_6$H$_3$—(OCOOCH$_2$C$_6$H$_5$)$_2$)C(O))$_1$, 2H), 2.10–1.36 (br d, —(NHCH((CH$_2$)$_3$CH$_2$NHCOOCH$_2$C$_6$H$_5$)—C(O))$_4$—(NH CH(CH$_2$C$_6$H$_3$(OCOOCH$_2$C$_6$H$_5$)$_2$)C(O))$_1$—, 4.8H). FTIR 1772 cm$^{-1}$ (nCO, vs), 1722 cm$^{-1}$ (nCO, vs), 1652 cm$^{-1}$ (Amide I, s br), 1543 cm$^{-1}$ (Amide II, s br). Elemental analysis: calcd for C$_{16.2}$O$_{3.8}$N$_{1.8}$H$_{18.6}$: C, 65.00; H, 6.26; N, 9.62 found C, 64.31; H, 6.46; N, 8.32.

Poly(L-lysine$_4$.HBr-L-DOPA$_1$), was generated as follows. To a solution of Poly(N$_e$-carbobenzyloxy-L-lysine$_4$-O, O'-dicarbobenzyloxy-L-DOPA$_1$), (1.1 g, 3.7 mmol ) in TFA (~10 ml), four equivalents of 33% HBr in acetic acid (w/w) was added with stirring. The mixture was stirred for one hour. The product was precipitated by addition of ether and then dried. The crude polymer was dissolved in small amount of water-methanol (1:4) and precipitated by addition of ether and dried in vacuo at room temperature overnight. The polymer were dissolved in water and isolated by freeze-drying as a white fluffy solid (0.74 g, 3.6 mmol 97%). $^1$H NMR (D$_2$O): d 7.52 (br s, —(NHCH((CH$_2$)$_3$CH$_2$NH$_2$·HBr) C(O))$_4$—(NHCH(CH$_2$C$_6$H$_2$H(OH)$_2$)C(O))$_1$—, 0.2H), 6.96–6.64 (br m, —(NHCH((CH$_2$)$_3$CH$_2$NH$_2$·HBr)C(O))$_4$—(NHCH(CH$_2$C$_6$H$_2$H(OH)$_2$)C(O))$_1$—, 0.4H), 4.36 (br s, —(NHCH((CH$_2$)$_3$CH$_2$NH$_2$·HBr)C(O))$_4$—(NHCH (CH$_2$C$_6$H$_2$H(OH)$_2$)C(O))$_1$—, 1H), 3.05 (br, s —(NHCH((CH$_2$)$_3$C H$_2$ NH$_2$ · HBr) Ct(O))$_4$ — (NHCH (CH$_2$ C$_6$H$_2$H(OH)$_2$) C(O))$_1$—, 2H), 2.05–1.30 (br, d —(NHCH((C H$_2$)$_3$CH$_2$NH$_2$·HBr)C(O))$_4$—(NHCH(CH$_2$C$_6$H$_2$H(OH)$_2$) C(O))$_1$—, 4.8H). Elemental analysis: calcd for C$_{6.6}$O$_{1.4}$N$_{1.8}$H$_{12.2}$Br$_{0.8}$: C, 39.03; H, 6.05; N, 12.41 found C, 42.86; H, 5.92; N, 10.08. The composition of the polymer was estimated by $^1$H NMR: the DOPA content was 19 mole % (by DOPA %=1-Lysine %, and lysine %=(integration (at 2.05–1.30)/3)/(integration (at 3.05)×100).

All the polymers were characterized using $^1$H NMR, FTIR, and elemental analysis. The percentage of L-DOPA in each copolymer was determined using a combination of $^1$H NMR and UV/vis absorption measurements at 280 nm. For example, the amount of L-DOPA, in poly(L-Lysine$_4$-L-Dopa) was found to be 19%. Data for representative polymers is given in Table 1.

TABLE 1

Polymer Synthesis

| Composition | Yield | M$_n$ | M$_w$/M$_n$ | H$_2$O soluble |
|---|---|---|---|---|
| Poly(CBZ-lysine), 3 | 94% | 147,000 | 1.42 | – |
| Poly(lysine$_9$.HBr), 4 | 97% | 103,000 | 1.45 | + |
| Poly(CBZ-lysine$_9$-DiCBZ-DOPA$_1$), 5 | 85% | 167,000 | 1.48 | – |
| Poly(lysine.HBr$_9$-DOPA$_1$), 6 | 88% | 120,000 | 1.52 | + |
| Poly(CBZ-lysine$_4$-DiCBZ-DOPA$_1$), 7 | 87% | 186,000 | 1.35 | – |
| Poly(lysine.HBr$_4$-DOPA$_1$), 8 | 97% | 113,000 | 1.39 | + |

These polymers were found to be soluble in aqueous buffers over wide pH ranges (ca 2–12). As disclosed in the examples below, we evaluated the ability of these polymer solutions to form crosslinked gels as functions of monomer composition, pH, and oxidizing agent. The oxidizing agents utilized were O$_2$, O$_2$/base, NaIO$_4$, H$_2$O$_2$, mushroom tyrosinase, and Fe(H$_2$O)$_6^{3+}$. The oxidizing agents were found (by NMR and UV/vis spectroscopy) to convert the catechol functionalities of the DOPA residues into o-quinone units which then self-condensed to form extensively crosslinked intractible solids. The products of self-condensation of simple o-quinone derivates were found to contain more than forty different species by TLC and HPLC analysis. With our L-DOPA containing copolypeptides, crosslinked gels or precipitates were formed upon oxidation in all cases.

Example 3

Control of Gellation Time Via Oxidizing Agent and pH

As an illustration of methods to control the properties of catechol containing adhesive copolymers, conditions utilizing different oxidizing agents under various pH schemes were used to effect the gellation times of different copolymer compositions. The results provided herein show that by manipulating conditions in this manner, adhesive copolymers with specific characteristics may be generated. Specifically, by varying the oxidizing agent and pH, gellation times can adjusted from seconds to days.

How specific combinations of different oxidizing agents and pH schemes may be used to control the gellation times of copolymer compositions is illustrated in Table 2 below. The times required for gel formation were determined by rheological measurements as described below;

ditions on adhesive forming ability, controlled lap shear tests were performed.

Adherends for lap shear studies were prepared in a number of ways. Aluminum adherends (5052-H32) were treated with a mixture of water, $H_2SO_4$ (conc.) and $Na_2Cr_2O_7$ (40:20:4) at 65~70° C. for 20 min. They were then rinsed with deionized water and air dried. Steel adherends (A366) were polished with sandpaper (220 grit), and then rinsed with hexane followed by acetone. Poly(methyl methacrylate) adherends were used without further treatment after removal of the protective paper coating from the clear plastic surface.

TABLE 2

Rheology Measurements.

| Oxidation conditions | Tyrosinase[a] | | pH = 12[b] | | NaIO$_4$[c] | | $H_2O_2$[d] | | Air (O$_2$) | |
|---|---|---|---|---|---|---|---|---|---|---|
| Time (min) | 0 | 48 | 0 | 4 | 0 | 3 | 0 | 6 | 0 | 180 |
| η* (Pa-s) | 0.004 | 0.047 | 0.118 | 0.196 | 0.082 | 0.085 | 0.005 | 0.144 | 0.008 | 0.198 |

The copolymer used was Poly(lysine.HBr$_4$-DOPA$_1$), M$_n$ = 126,000. a = 300 units of enzyme were added of a pH = 7 phosphate buffer solution (0.01N phosphate). b = 0.01N phosphate buffer. c = 0.04N solution. d = 1.5 wt % solution. The two time points represent the beginning of the experiment and the gelation point.

Example 4

Control of Viscosity Via Oxidizing Agent and pH

As an illustration of methods to control the properties of catechol containing adhesive copolymers, conditions utilizing different oxidizing agents under various pH schemes were used to effect the viscosity of different copolymer compositions. The results provided herein show that by manipulating conditions in this manner, adhesive copolymers with specific characteristics may be generated. Specifically, by varying the oxidizing agent and pH, viscosity as a function of time may be controlled.

How specific combinations of different oxidizing agents and pH schemes may be used to control the viscosity of copolymer compositions is illustrated in Table 2 below. To measure curing time and viscosity, the rheological behavior of solutions of Poly(L-lysine$_4$·HBr-L-DOPA$_1$) under different conditions was studied using a Rheometrics ARES Rheometer at room temperature. A cone and plate geometry was used in a dynamic time sweep experiment at a frequency of 2.0 rad/s and at 100% strain. The concentration of each polymer solution was 2.5 mg/ml. The viscosity of each adhesive mixture solution was measured as a function of time. The two time points are the beginning of the experiment and the gelation point.

Example 5

Control of Adhesive Properties Via Oxidizing Agent and pH

As an illustration of methods to control the properties of catechol containing adhesive copolymers, conditions utilizing different oxidizing agents under various pH schemes were used to effect the adhesive strength of different copolymer compositions. The results provided herein show that by manipulating conditions in this manner, adhesive copolymers with specific characteristics may be generated. Specifically, by varying the oxidizing agent and pH, adhesive copolypeptides having differing adhesive properties may be generated. To measure the effects of different con- In order to prepare the test sample preparation, the adhesive polymer solution is spread on both adherend slides, which were then overlapped with two Cu wires (0.06 mm diameter) placed as spacers between the adhesive joint. The overlapped samples were clamped together for about 3 hours to prevent motion and kept in a temperature controlled oven for the specified time period.

The tensile strength of samples as prepared above was measured at room temperature with an Instron 1123 Mechanical Testing Apparatus according to the ASTM D1002 method. An Instron 5000 Lb reversible load cell was used for the measurements. *Data acquisition & control version* 3.00 (©1994 University of California Santa Barbara) was used to monitor the data output. The adherend size was 4 in by 1 in, the loading rate was 0.05 in/min, bond line thickness was 0.06 mm, and the area of the bond was 0.39 in$^2$. Three samples were measured for each experiment and the average of these values was reported.

How specific combinations of different oxidizing agents and pH schemes may be used to control the adhesive strength of copolymer compositions is illustrated in Table 3 below.

TABLE 3

| | Lap Shear Test[a] | | | | | |
|---|---|---|---|---|---|---|
| Oxidation | Aluminum | | | | | Steel |
| conditions | Air | $H_2O_2$[a] | pH7[b] | pH12[b] | Tyrosinase/pH7[c] | Air |
| 4(144K) | 0.58 | 0.61 | 0.49 | 0.65 | 0.56 | 0.44 |
| 6(242K) | 2.52 | 2.39 | 2.24 | 3.45 | 2.81 | 3.36 |
| 8(255K) | 4.32 | 4.29 | 4.02 | 3.75 | 4.70 | 4.00 |

Adhesive strengths (MPa) of polymers as a function of composition under different oxidizing conditions at 35° C. for one day. Polymer concentration = 40 mg/100 μL. Polymer molecular weight is given in parentheses.
[a] = the amount of $H_2O_2$ (0.3 wt %) used was 0.5 mL/g polymer.
[b] = final concentration of phosphate buffer was 0.025 M.
[c] = the concentration of enzyme was 5 units/mg polymer.

Example 6

Control of Adhesive Strength Via Oxidizing Agent and Polymer Concentration

As an illustration of methods to control the properties of catechol containing adhesive copolymers, conditions utilizing different oxidizing agents and polymer concentrations were used to effect the adhesive strength of different copolymer compositions. The results provided herein show that by manipulating conditions in this manner, adhesive copolymers with specific characteristics may be generated. Specifically, by varying the oxidizing agent and polymer concentration, adhesive copolypeptides having differing adhesive properties may be generated. To measure the effects of different conditions on adhesive forming ability, controlled lap shear tests as described above were performed.

Using poly(L-lysine) as a model, we examined different L-lysine/L-DOPA binary copolymers. The copolymers were tested under a variety of oxidizing conditions and were found to form moisture-resistant adhesive bonds under all conditions. The use of chemical oxidants allowed bond formation in a matter of seconds, while enzymatic and aerobic oxidation gave cured samples in hours and days. Using dilute hydrogen peroxide we were able to form adhesive bonds to steel adherends which increased in strength with polymer concentration (Graph 1 below).

Measurements on different adherents with our optimized conditions also showed formation of moisture-resistant bonds. The best systems for adhesive formation are partially substrate specific. Polymer containing 20 mole percent L-DOPA generally gives the strongest bonds, especially when dissolved in phosphate buffer (0.25M). $H_2O_2$ is generally the best oxidizing agent, except that low concentrations need to be used on metals and plastics, or when slow oxidation is desired.

Example 7

Control of Adhesive Strength Via Oxidizing Agent, pH and Polypeptide Composition As an illustration of methods to control the properties of catechol containing adhesive copolymers, conditions utilizing different oxidizing agents under various pH schemes were used to effect the adhesive strength of different copolymer compositions. The results provided herein show that by manipulating conditions in this manner, adhesive copolymers with specific characteristics may be generated. Specifically, by varying the oxidizing agent and pH, adhesive copolypeptides having differing adhesive properties may be generated. To measure the effects of different conditions on adhesive forming ability, controlled lap shear tests as described above were performed.

Adherends were prepared in a number of ways. Aluminum adherends (5052-H32) were treated with a mixture of water, $H_2SO_4$ (conc.) and $Na_2Cr_2O_7$ (40:20:4) at 65~70° C. for 20 min. They were then rinsed with deionized water and air dried. Steel adherends (A366) were polished with sandpaper (220 grit), and then rinsed with hexane followed by acetone. Poly(methyl methacrylate) adherends were used without further treatment after removal of the protective paper coating from the clear plastic surface.

In order to prepare the test sample preparation, the adhesive polymer solution (40 mg/100 mL solvent) was spread on both adherend slides, which were then overlapped with two Cu wires (0.06 mm diameter) placed as spacers between the adhesive joint. The overlapped samples were clamped together for about 3 hours to prevent motion and kept in a temperature controlled oven for the specified time period.

The tensile strength of samples as prepared above was measured at room temperature with an Instron 1123 Mechanical Testing Apparatus according to the ASTM D1002 method. An Instron 5000 Lb reversible load cell was used for the measurements. *Data acquisition & control version* 3.00 (©1994 University of California Santa Barbara) was used to monitor the data output. The adherend size was 4 in by 1 in, the loading rate was 0.05 in/min, bond line thickness was 0.06 mm, and the area of the bond was 0.39 $in^2$. Three samples were measured for each experiment and the average of these values was reported.

As an illustration of how the properties of the adhesive copolymers may be controlled by curing of the adhesive with air ($O_2$), a solution of adhesive polymer, poly(L-$Lys_4$·HBr-$Dopa_1$) of defined molecular weight, in deionized water (40 mg/100 mL) was spread on both adherend slides, e.g., aluminum, which were then overlapped with two Cu wires (0.06 mm diameter) placed as spacers between the adhesive joint. The overlapped samples were clamped together to prevent movement for about 3 hours, and kept in a temperature controlled oven vented to the air, e.g., at 40° C., for a specified time period, e.g., 24 hours. The samples were then removed from the oven and the adhesive tensile bond strength measured on the Instron as described above. Bond strength is given in Table 3 (4.32 MPa for 40° C. on aluminum for 24 hours using a 255,000 molecular weight polymer).

As an illustration of how the properties of the adhesive copolymers may be controlled by curing of the adhesive with air and base ($O_2$-pH=12), a solution of adhesive polymer, poly(L-$Lys_4$·HBr-$Dopa_1$) of defined molecular weight, in deionized water (80 g/100 mL) was mixed with an equal volume of 0.050M phosphate buffer at pH=12 and then spread on both adherend slides, e.g., aluminum, which were then overlapped with two Cu wires (0.06 mm diameter) placed as spacers between the adhesive joint. The overlapped samples were clamped together to prevent movement for about 3 hours, and kept in a temperature controlled oven vented to the air, e.g., at 40° C., for a specified time period, e.g., 24 hours. The samples were then removed from the oven and the adhesive tensile bond strength measured on the Instron as described above. Bond strength is given in Table 3 (3.75 MPa for 40° C. on aluminum for 24 hours using a 255,000 molecular weight polymer).

As an illustration of how the properties of the adhesive copolymers may be controlled by curing of the adhesive with phosphate buffer ($O_2$-pH=7), a solution of adhesive polymer, poly(L-$Lys_4$·HBr-$Dopa_1$) of defined molecular weight, in deionized water (80 g/100 mL) was mixed with an equal volume of 0.050M phosphate buffer at pH=7 and then spread on both adherend slides, e.g., aluminum, which were then overlapped with two Cu wires (0.06 mm diameter) placed as spacers between the adhesive joint. The overlapped samples were clamped together to prevent movement for about 3 hours, and kept in a temperature controlled oven vented to the air, e.g., at 40° C., for a specified time period, e.g., 24 hours. The samples were then removed from the oven and the adhesive tensile bond strength measured on the Instron as described above. Bond strength is given in Table 3 (4.02 MPa for 40° C. on aluminum for 24 hours using a 255,000 molecular weight polymer).

As an illustration of how the properties of the adhesive copolymers may be controlled by curing of the adhesive with hydrogen peroxide, a solution of adhesive polymer, poly(L-Lys$_4$·HBr-Dopa$_1$) of defined molecular weight, in deionized water (40 g/100 mL) was mixed with 0.3% aqueous hydrogen peroxide solution (0.5 ml/mg polymer) and then spread on both adherend slides, e.g., aluminum, which were then overlapped with two Cu wires (0.06 mm diameter) placed as spacers between the adhesive joint. The overlapped samples were clamped together to prevent movement for about 3 hours, and kept in a temperature controlled oven vented to the air, e.g., at 40° C., for a specified time period, e.g., 24 hours. The samples were then removed from the oven and the adhesive tensile bond strength measured on the Instron as described above. Bond strength is given in Table 3 (4.29 MPa for 40° C. on aluminum for 24 hours using a 255,000 molecular weight polymer).

As an illustration of how the properties of the adhesive copolymers may be controlled by curing of the adhesive with iron oxide, a solution of adhesive polymer, poly(L-Lys$_4$·HBr-Dopa$_1$) of defined molecular weight, in deionized water (40 g/100 mL) was spread on both steel adherend slides, which were then overlapped with two Cu wires (0.06 mm diameter) placed as spacers between the adhesive joint. The iron oxide present on the steel surface caused rapid oxidation of the copolymer. The overlapped samples were clamped together to prevent movement for about 3 hours, and kept in a temperature controlled oven vented to the air, e.g., at 40° C., for a specified time period, e.g., 24 hours. The samples were then removed from the oven and the adhesive tensile bond strength measured on the Instron as described above. Bond strength is given in Table 3 (4.00 MPa for 40° C. on steel for 24 hours using a 255,000 molecular weight polymer).

Example 8

Control of Adhesive Strength Using Different Copolypeptide Substrates, Oxidizing Agents and Concentration of Hydrogen Peroxide, Curing Times, Temperature and Molecular Weight As an illustration of methods to control the properties of catechol containing adhesive copolymers, reaction conditions utilizing different copolypeptide substrates, oxidizing agents and concentrations of oxidizing agents, curing times, temperature, copolymer concentration and molecular weight were generated as means to effect the adhesive strength of these copolymers. The results provided herein show that by manipulating conditions in this manner, adhesive copolymers with specific characteristics may be generated. Specifically, by varying these conditions, adhesive copolypeptides having differing adhesive properties may be generated. To illustrate the effects of different conditions on adhesive strength, controlled lap shear tests as described above were performed.

The results of these studies are provided in Tables 4–8 below. Table 4 illustrates the effects of different substrates on adhesive strength. Table 5 illustrates the effects of oxidizing agents and concentration of the oxidizing agent hydrogen peroxide, on adhesive strength. Table 6 illustrates the effects of time on adhesive strength. Table 7 illustrates the effects of temperature on adhesive strength. Table 8 illustrates the effects of molecular weight on adhesive strength.

TABLE 4

Adhesive strengths (MPa) of poly(L-Lys$_4$·HBr-Dopa$_1$)(M$_n$ = 98K) on different substrates in aqueous solution at 40° C. for one day. Polymer concentration = 40 mg/100 mL H$_2$O.

| Substrate | aluminum | steel | PMMA | Glass |
|---|---|---|---|---|
| Tensile Strength | 1.75 | 1.52 | 0.32 | 0.71 |

TABLE 5

Adhesive strength (MPa) of poly(L-Lys$_4$·HBr-Dopa$_1$)(M$_n$ = 98K) as a function of peroxide concentration at 35° C. on aluminum. Polymer concentration = 40 mg/100 mL H$_2$O.

| Oxidizing Conditions | H$_2$O | .3% H$_2$O$_2$* | 1% H$_2$O$_2$* | 5% H$_2$O$_2$* |
|---|---|---|---|---|
| Poly(L-Lys$_4$·HBr-Dopa$_1$)(3h) | .16 | .41 | .66 | 0.70 |
| Poly(L-Lys$_4$·HBr-Dopa$_1$)(6h) | .85 | .78 | | |

*The amount of H$_2$O$_2$ solution used was .5 ml/mg polymer

TABLE 6

Adhesive strength (MPa) of poly(L-Lys$_4$·HBr-Dopa$_1$), M$_n$ = 186 K, as a function of time in aqueous solution at room temperature on steel. Polymer concentration = 40 mg/100 mL H$_2$O.

| Time | 1h | 2h | 6h | 12h | 24h |
|---|---|---|---|---|---|
| Tensile Strength | 0.124 | 0.186 | 1.13 | 2.75 | 2.52 |

TABLE 7

Effects of temperature on the adhesive strength (MPa) of poly(L-Lys$_4$·HBr-Dopa$_1$) (M$_n$ = 98K) at a concentration of 40 mg/100 mL H$_2$O on steel for one day.

| Temperature | 20° C. | 40° C. | 60° C. |
|---|---|---|---|
| Tensile Strength | 0.72 | 1.52 | 1.48 |

TABLE 8

Adhesive strengths (MPa) of poly(L-Lys$_4$·HBr-Dopa$_1$) as a function of molecular weight in H$_2$O at 40° C. on steel for one day.

| Molecular Weight | 98K | 186K | 255K |
|---|---|---|---|
| Tensile Strength | 1.52 | 2.52 | 4.00 |

What is claimed is:
1. A method of crosslinking a catechol containing polypeptide comprising the steps of:
   (a) exposing the catechol containing polypeptide to an inorganic chemical oxidizing agent within a reaction environment;
   (b) controlling a first condition within the reaction environment, wherein the condition is selected from the group consisting of type of inorganic chemical oxidizing agent, amount of inorganic chemical oxidizing agent, and a pH of about 7 to about 12, to modulate a characteristic of the crosslinked catechol containing polypeptide, wherein the modulated characteristic is selected from the group consisting of adhesive strength, gellation time and viscosity.
2. The method of claim 1, wherein the characteristic is viscosity or gellation time.

3. The method of claim 2 wherein the type of inorganic chemical oxidizing agent is selected from the group consisting of oxygen, peroxide, periodate, and ferric ion.

4. The method of claim 1, wherein the characteristic of the crosslinked catechol containing polypeptide is modulated by controlling the type of inorganic chemical oxidizing agent, wherein the type of inorganic chemical oxidizing agent is selected from the group consisting of oxygen, peroxide, periodate, and ferric ion.

5. The method of claim 4 wherein the type of inorganic chemical oxidizing agent is oxygen and the pH is about 7 to about 12.

6. The method of claim 5, wherein the pH is about 12.

7. The method of claim 1, wherein the characteristic is adhesive strength.

8. The method of claim 7, wherein the adhesive strength of the crosslinked catechol containing polypeptide is modulated by controlling a second condition within the reaction environment selected from the group consisting of polypeptide monomer composition, polypeptide molecular weight, polypeptide concentration, temperature, curing time, and substrate with which the crosslinked catechol containing polypeptide interacts.

9. The method of claim 8, wherein the adhesive strength is modulated by controlling the substrate with which the crosslinked catechol containing polypeptide interacts.

10. The method of claim 9, wherein the polypeptide substrate is selected from the group consisting of aluminum, steel and glass.

11. The method of claim 8, wherein the catechol containing polypeptide is a synthetic polypeptide.

12. The method of claim 11 wherein the catechol containing polypeptide is a binary copolypeptide.

13. The method of claim 11 wherein the synthetic polypeptide is a copolypeptide having a monomer composition of at least 10 mole percent L-Dopa.

14. The method of claim 13 wherein the monomer composition of the copolypeptide is about 20 mole percent L-Dopa.

* * * * *